United States Patent [19]

Adler

[11] Patent Number: 4,487,581
[45] Date of Patent: Dec. 11, 1984

[54] ORTHODONTIC BRACKET

[76] Inventor: Theodore Adler, 146 Soundview Ave., White Plains, N.Y. 10605

[21] Appl. No.: 429,201

[22] Filed: Sep. 30, 1982

[51] Int. Cl.³ .............................................. A61C 7/00
[52] U.S. Cl. .................................................... 433/16
[58] Field of Search .................................. 433/11, 16

[56] References Cited

U.S. PATENT DOCUMENTS 2,908,974  10/1959  Stifter ................................. 433/16
3,946,488  3/1976  Miller et al. ........................ 433/11

Primary Examiner—Robert Peshock
Attorney, Agent, or Firm—Lackenbach, Siegel, Marzullo, Presta & Aronson

[57] ABSTRACT

An improved orthodontic bracket is formed of a wire gripping block secured within a spring metal base having wings or string tabs which set within tab receiving slots on opposite ends of the block. A slot within the face of the block is configured for gripping an orthodontic banding or arch wire extending from tooth to tooth, the face being large enough to accommodate any desired orientation of the slot to convert tension forces in the wire to a desired amount of torque for inducing a predetermined rotation of the tooth. A central plate portion of the base includes a slot elongated for the guidance of an orthodontic pin between the block and the base while transverse wing portions of the aperture serve as keyways for cooperation with alignment pins extending from a back face of the block. A channel for receipt of the orthodontic pin is also located on the back face of the block. A bifurcated shim having legs contacting cam surfaces of the block for insertion between the block and the base to facilitate removal of the block for interchanging with other blocks, the legs passing outside the alignment pins and one of the tabs, the one tab having peripheral slots for engagement with the legs.

14 Claims, 13 Drawing Figures

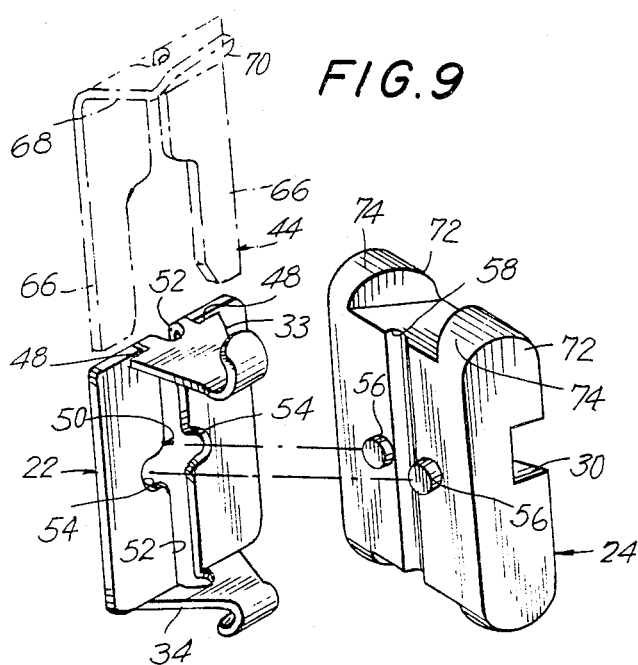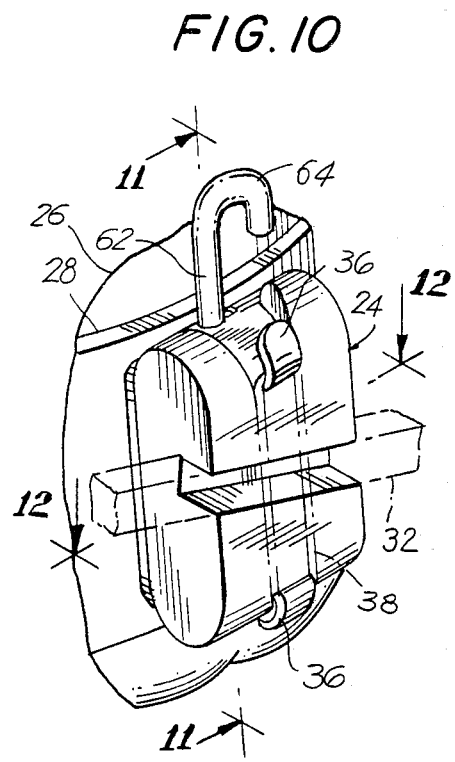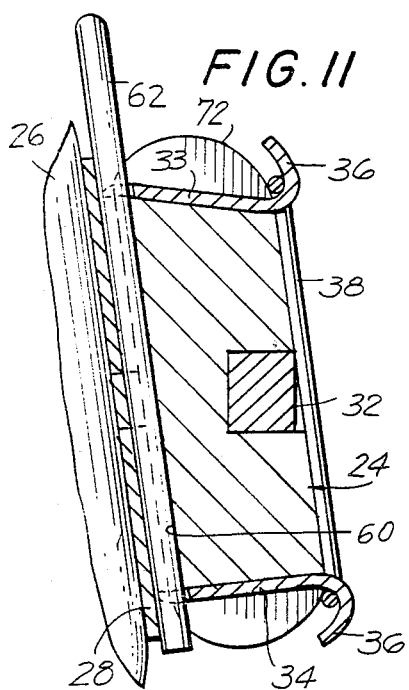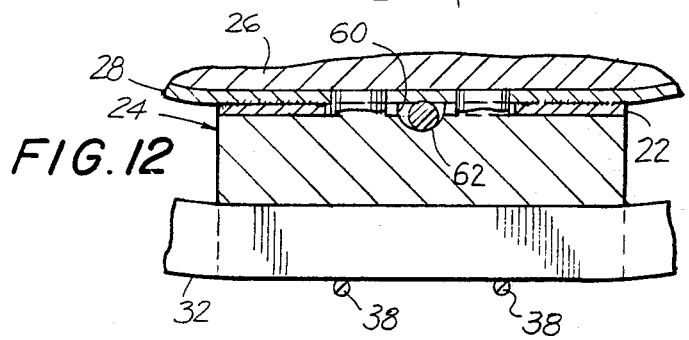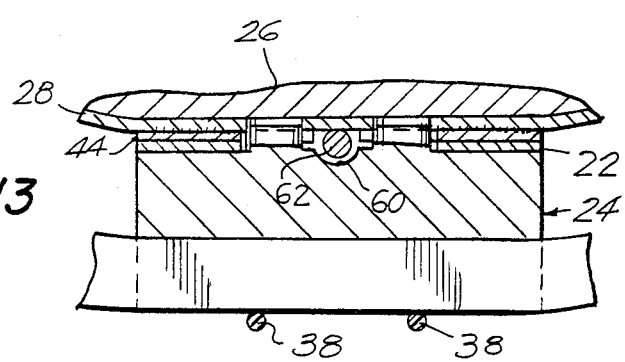

४,४८७,५८१

ORTHODONTIC BRACKET

BACKGROUND OF THE INVENTION

This invention relates to orthodontic equipment and, more particularly, to an improved orthodontic bracket for securing wires to teeth.

Brackets and wire are utilized in orthodontic procedures for the positioning of teeth. The brackets are secured to the teeth, and the wire is secured to the brackets. The brackets gripping the wire so as to transmit forces of wire twist and forces of wire bends as torques for rotating the teeth about various axis as well as for introducing linear translations to the respective positions of the teeth. The brackets may be secured to the teeth by conventional means, such as by adhesives or they may be secured to or form part of a band attached about a tooth.

With respect to the construction of the brackets, a multiple-sectioned bracket has advantages over a unitary one-piece monolithic bracket. For example, a multiple-sectioned bracket may be constructed of a base member which is secured to the tooth, and a block which is supported by the base and, in turn, is adapted for gripping a wire. Such a two-piece bracket is advantageous in that the wire supporting block may be replaced for a revised gripping of the wire without a disconnection of the bracket base from the tooth.

A problem arises in that while multiple sectioned brackets have been proposed, to date, no such bracket has proven successful in actual dental practice for a variety of reasons, including failure of adequate alignment between block and base, as well as difficulty in the disengagement of the block from the base. As a result, orthodontists and dentists have avoided the use of such multiple sectioned brackets due to the difficulty in obtaining the adequate accuracy of alignment, and due to the inconvenience experienced in the separation of block from base of the multiple-sectioned brackets.

The following U.S. patents are believed to be exemplary of the state-of-the-art of orthodontic brackets: U.S. Pat. No. 3,477,127; U.S. Pat. No. 3,660,900; U.S. Pat. No. 2,908,974; U.S. Pat. No. 4,186,488; U.S. Pat. No. 3,464,112; U.S. Pat. No. 3,464,113; U.S. Pat. No. 4,186,488; U.S. Pat. No. 4,244,898; U.S. Pat. No. 4,107,844; U.S. Pat. No. 3,964,165; U.S. Pat. No. 4,249,897; U.S. Pat. No. 3,930,311; U.S. Pat. No. 3,335,496; U.S. Pat. No. 3,946,488; U.S. Pat. No. 4,249,897; U.S. Pat. No. 3,881,252.

Of the foregoing patents, U.S. Pat. No. 2,908,974 of Stifter is of particular interest. Stifter discloses an anchor bracket of uniform size for each of a set of teeth and which is adapted to receive copy of a set of socket members having configurations for different wires. However, Stifter's bracket is to be entered from the side for insertion of a socket, this presenting an apparent difficulty when fixtures on neighboring teeth block such insertion.

Also of interest is U.S. Pat. No. 4,249,897 of Anderson which discloses inner and outer brackets, the inner bracket being deformable for the release of force associated with the wires interconnecting the brackets in a set of teeth.

The foregoing and other problems are overcome and other advantages are provided by an orthodontic bracket incorporating the invention, the bracket providing for precise alignment with the tooth and in the gripping of the wire as well as for facile engagement and disengagement from an outer or base element secured to the tooth. In accordance with the invention, the bracket comprises a wire gripping inner element block and a base to which the block is secured by spring tabs and alignment pins. As used herein, the term wire as understood includes any form of band, whether of metallic or non-metallic material.

Two spring tabs extend from the base, one tab being above the block and the other tab being below the block. The upper tab is provided with peripheral slots adjacent the base by which a U-shaped shim may be inserted between the base and the block for displacing the block from the base to release the tabs from the block. A pair of alignment pins extend from the rear of the block for insertion into correspondingly positioned alignment apertures within the base. The pins serve as a key and the apertures serve as a keyway for receipt of the key to provide for immediate alignment upon assembly of the base and block of the bracket. The foregoing arrangement facilitates manufacture of the bracket since the base can be fabricated of spring steel while any manufacturing tolerances are automatically compensated by the keying of the block to the base. The block being formed as a unitary monolithic structure, is readily manufactured by a molding operation, and may be suitably fabricated from a plastic material.

BRIEF DESCRIPTION OF THE DRAWINGS

The foregoing features and other aspects of the invention will be explained in greater detail when the following description is read and taken in connection with the accompanying drawings wherein:

FIG. 9 is an exploded view of the bracket including the shim shown in phantom, the Figure also showing the positioning of the alignment pins, and a channel in the rear face of the block for receipt of a pin;

FIG. 10 is an isometric view of the bracket of FIG. 9 with a pin inserted in the channel of the block;

FIG. 11 is a sectional view of the bracket taken along the line 11—11 in FIG. 10;

FIG. 12 is a sectional view of the bracket taken along the line 12—12 in FIG. 11; and FIG. 13 is a sectional view similar to that of FIG. 12, but further including the shim of FIG. 9 preparatory to disengagement of the block from the base.

DESCRIPTION OF THE PREFERRED EMBODIMENT

Figure 1:
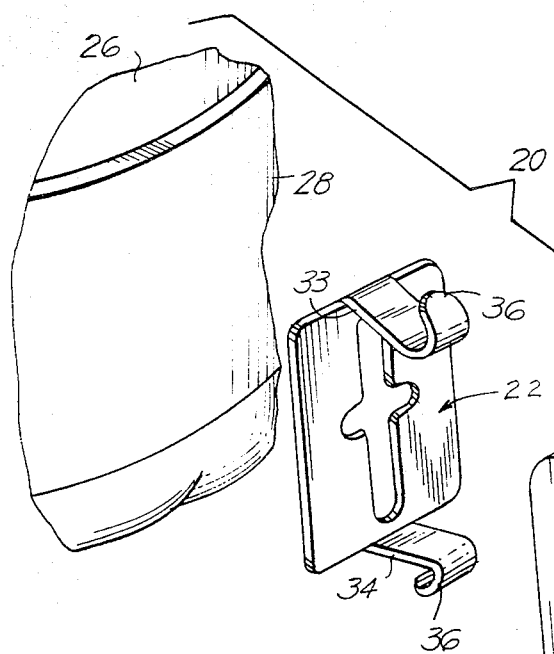
FIG. 1 is an exploded view of the two-piece bracket of the invention and a tooth to which the bracket is to be secured as by means of an exemplary band.
Figure 2:
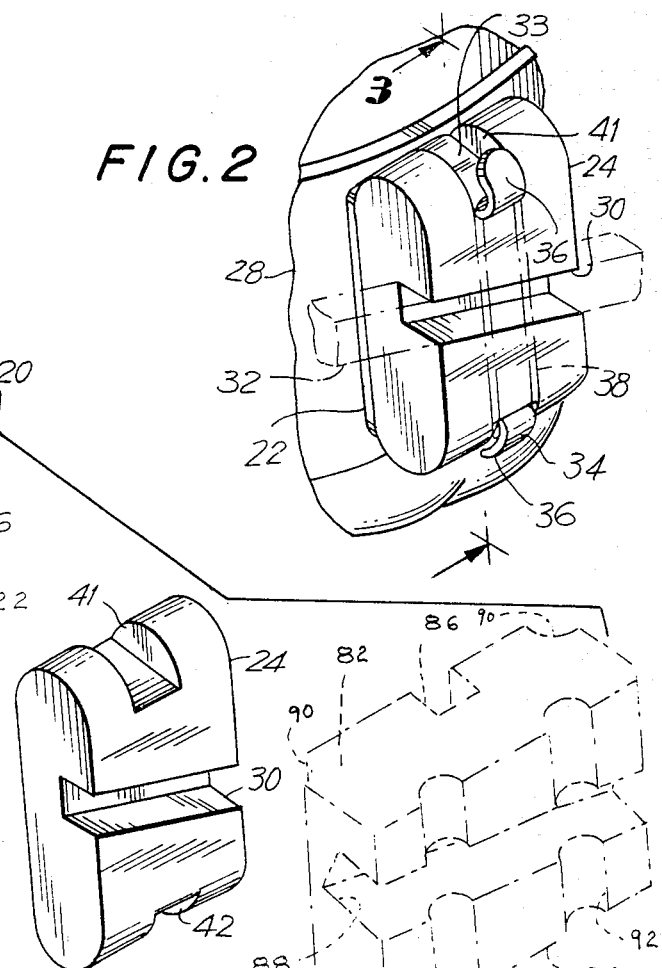
FIG. 2 shows the bracket of FIG. 1 secured to the tooth, and a wire carried by a slot in the block of the bracket is shown in phantom.
Figure 3:
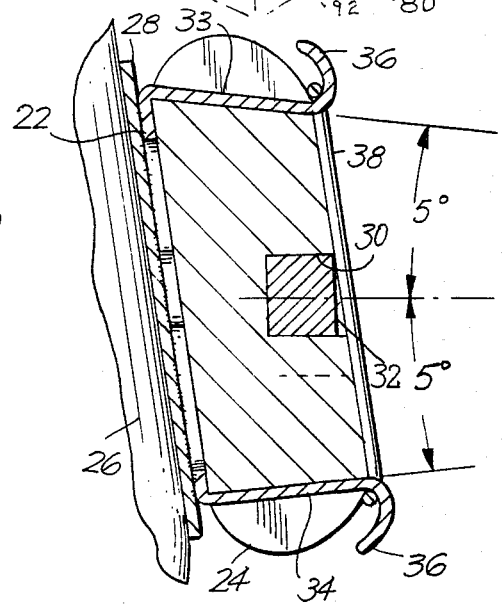
FIG. 3 is a sectional view of the bracket taken along the line 3—3 in FIG. 2, the view including a rubber band for securing tabs of a base of the bracket about the block.

Referring now to the drawings, and in particular to FIGS. 1-3, there is shown a bracket 20 constructed in accordance with the invention. The bracket comprises a base 22 and a block 24. The bracket is to be secured to a tooth 26 either by an adhesive or by means of a band, an exemplary band 28 being shown for securing the bracket 20 to the tooth 26. The block 24 has a slot 30 in the front face thereof for engagement with an arch wire 32, shown in phantom, by which forces are developed in a patient's mouth for the movement of teeth in multiple directions. The base 22 includes a pair of opposite wings or tabs 33-34 which are manufactured so as to be bent over the block 24 to secure the block to the base 22, the tabs 33-34 terminating in ears 36 for receiving an elastic member, such as rubber band 38 by which the tabs 33-34 may be tied down and tightly gripped about the block 24.

Figure 5:
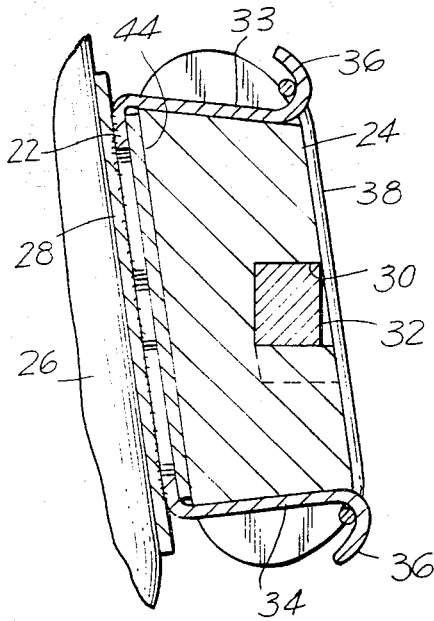
FIG. 5 is a sectional view of the bracket, similar to that of FIG. 3, the view of FIG. 5 further including a shim between the block and the base.

The block 24 is of unitary monolithic construction which may be readily molded of a suitable plastic material to include slots 41-42 at the top and the bottom of the block 24 for receipt of the tabs 33-34 for accurate positioning of the block 24 within the base 22. An advantage of my inner-outer bracket assembly is that the block can be inserted into the base from the front directly and not from either side of the base. Such arrangement enables blocks for any tooth to be easily placed on their respective bases. Such an arrangement clearly aids the orthodontist in properly positioning the outer or base element when he is cementing it in place on a tooth. The slots 41 and 42 are angled with respect to the base 22 as are the tabs 33 and 34 similarly inclined for retaining the block 24 in the grip of the tabs 33-34. As shown in FIG. 5, a bisecting plane through the center of the block and base forms an angle, preferably of about 5° with the tabs 33,34. With all teeth in an "ideal" position, and bisecting planes are parallel to each other, the angle the wings or the tabs form with the base varies from tooth to tooth. On the other hand, with bisecting planes not parallel, the wings or tabs would form the same angle to the base each time. The arch wire slot 30 may be level or inclined dependent on torque, that is whether a torque is to be applied to the tooth 26. The inclination of the slot 30 as shown in the figures provides for a torque which tends to rotate the tooth towards, or from, the vertical position.

Figure 4:
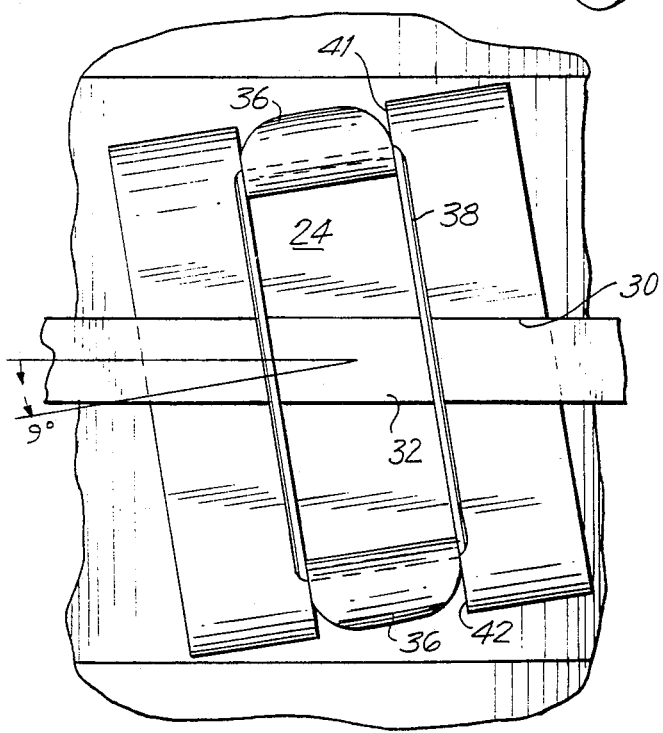
FIG. 4 is a front elevation view of the bracket of FIGS. 1-3 with an exemplary mounting angled relative to the axis of the tooth.

With reference to FIGS. 4-7, alternative configurations in the use of the bracket are shown. In FIG. 4, the bracket 20 has been secured to the tooth and/or band 28 in an angled orientation of 9°, the bracket having been rotated about the vertical axis and about the normal to the tooth surface to provide for a rotation of the tooth about its vertical axis without a further tilting of the tooth either towards or away from its vertical axis.

Figure 6:
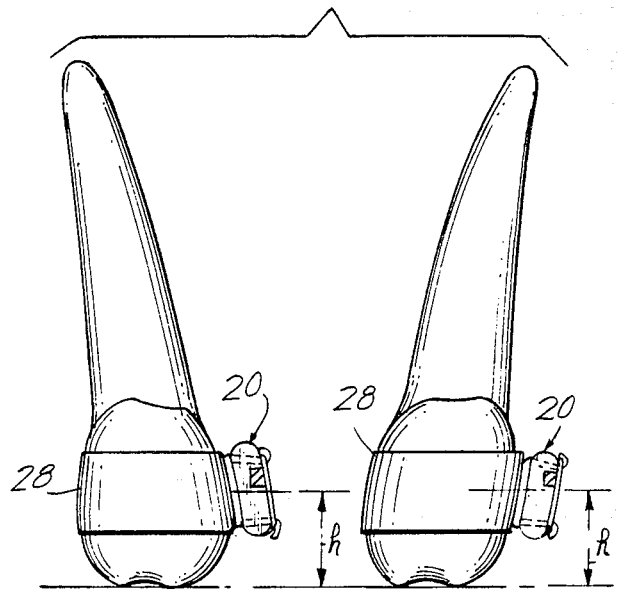
FIG. 6 is an exemplary view of two teeth having different geometries of orientation with brackets secured thereto; but with the same elevation height from common bottom tooth line to relative outer of the tooth.
Figure 7:
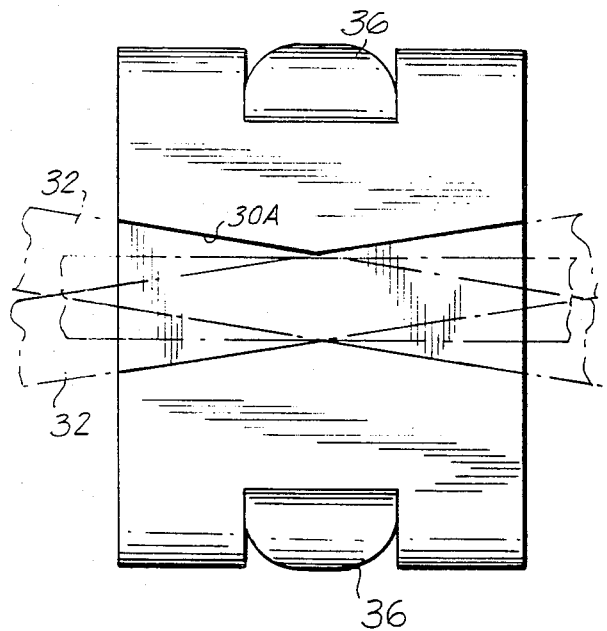
FIG. 7 is a front elevation view of a modified bracket embodying an exemplary block with a doubly divergent slot.

In FIG. 5, there is shown the use of a shim 44 placed between the block 24 and the base 22 resulting in a displacement of the block 24 away from the base 22. Such use of the shim 44 facilitates extraction of the block 24 from the base 22. FIG. 6 simply illustrates that since the center of the base bracket on the outside is also the center of the base bracket on the inside, the heights (h) of individual teeth, which ideally should be the same, are more readily adjusted while achieving the axial inclination required for each individual tooth. In other words, the tabs of the outer element if bisected with an imaginary plane also bisecting the base of the bracket, regardless of how the base has been inclined, would exhibit for each tooth, the bisection of the angle of convergence of the tabs would, if all the teeth were to be in ideal occlusion, they create a plane that would be essentially identical to the bisector plane of every other bracket assembly for every tooth in the dental arch of one's mouth. In FIG. 7, the bracket has been modified by the provision of a doubly divergent slot 30A. The shape of the slot 30A which is in the form of an X precludes the development of a tilting torque upon the tooth by the wire 32. This is demonstrated in FIG. 7 by three possible positions of the wire 32, shown in phantom, wherein the slot 30A permits an inclination of the wire 32 without a corresponding tilting of the bracket.

Figure 8:
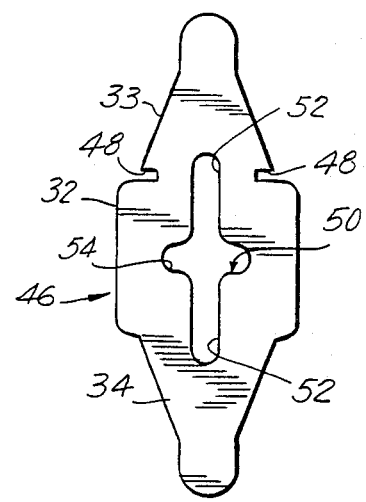
FIG. 8 is a plan view of the base element shown as a flat plate prior to the bending of the tabs.

Referring now to FIG. 8, the base is shown as a flat plate 46 prior to the bending of the tabs 33-34. Peripheral slots 48 are located at the inner end of the tab 33 adjacent the base 22 to provide access for the shim 44, as will be described further with reference to FIG. 9. The plate 46 has a central aperture 50, portions of which are shaped as legs 52 to accommodate a pin, as will be described further with reference to FIG. 10, the aperture 50 also having wings 54 to accommodate alignment pins as will be described further with reference to FIG. 9.

Referring now to FIGS. 9-13, the block 24 includes a pair of alignment pins 56 and a vertically disposed channel 58 located on the rear face of the block 24. Upon insertion of the block 24 within the base 22, the pins 56 slide within the wings 54 of the aperture 50, and the channel 58 abuts the legs 52 of the aperture 50. The alignment pins 56 and the wings 54 thus serve as keys and keyways, respectively, for accurately keying the position of the block 24 of the base 22. The aperture 50 in cooperation with the channel 58 serve as a guide 60 for holding an orthodontic pin 62 having a hook 64 which sets above the bracket 20. The hook 64 provides a convenient tie point for further interconnection of the brackets on the respective teeth, as by resilient means, such as rubber bands (not shown), in an orthodontic procedure.

The shim 44 is bifurcated into two legs 66 joined by a wing 68 extending generally perpendicularly to the legs 66 and terminating in an ear 70 for easy manipulation by a dentist. In operation, the shim 44 is inserted between the block 24 and the base 22 to effect a separation of the block 24 from the base 22, the insertion being accomplished by passing the legs 66 through suitable slots 48 of the base tab 33. To facilitate the insertion of the legs 66 with the accompanying wedging action of the shim 44, the block 24 is provided with ears 72 which bound the slot 41 and have rounded cam surfaces 74 against which the legs 66 of the shim 44 are pressed to wedge apart the block 24 from the base 22. Such a wedging displaces the block 24 forward of the base 22, thereby releasing the grips of the resilient tabs 33-34 allowing the facile removal of the block 24 from the base 22. It is also noted that the leg 52 in the upper portion of the base aperture 50 extends into the tab 33, and similarly the bifurcation of the shim 44 extends into the wing 68, to provide access for the orthodontic pin 62. Accordingly, the shim 44 can be inserted both in the presence and in the absence of the pin 62.

Moreover, the bracket 20 can be readily attached to a tooth, and the block 24 can be readily separated from the base 22 for an interchanging of blocks 24 at various stages in an orthodontic procedure. The interchanging of blocks permits blocks of differing slot configurations to be utilized. For example, the slots may be positioned at different elevations and may be inclined at different inclinations or oriented at different twist angles about the vertical axis for developing a variety of twisting and rotating torques as well as displacement forces for repositioning a tooth. The shim 44 permits the block 24 to be removed easily as by "popping out" the tooth with the wedging action of the shim 44. Also, the channel 58 in the back face of a block 24 in cooperation with the elongated configuration of the base aperture 50 and the bifurcated configuration of the shim 44 permits insertion of the pin 62 for the further interconnection among the teeth to aid in their repositioning.

It is also noted that the block 24 can be constructed in an alternative form of block, identified by the legend 80 and shown in phantom in FIG. 1. The block 80 has top and bottom surfaces 82 and 84 for contacting the ears 36 of the base 22. (Only the front edge of the surface 84 is visible in the drawing). A channel 86 at the rear of the block 80 is provided for receiving a pin such as the pin 62. A slot 88 on the front face of the block 80 receives a wire as does the slot 30 in the block 24. By way of example, the slot 88 is shown tilted in two planes, in both the vertical plane and the horizontal plane to provide a torque to the tooth 26 about two orthogonal axes. The slot is also tilted about its axis for a twisting torque. Longitudinal recesses 90 are provided at the back corners of the block 80 to facilitate a manual gripping of the block 80 for placement on and removal from the band 28. Front channels 92 provide for a recessed position for a rubber band, such as the band 38 for holding a wire, such as the wire 32 in the slot 88. The block 80 has a greater length than the block 24 and, accordingly, its slot 88 is of greater length than the slot 30 for exertion of greater torque. Use of both blocks 24 and 80 permits differing amounts of torque to be applied to the teeth, over a greater range of torque, than can be applied by use of only one of the blocks 24 or 80.

Although the present invention has been described in some detail by way of illustration and example for purposes of clarity of understanding, it will, of course, be understood that various changes and modifications may be made in the form, details and arrangements of the parts without departing from the scope of the invention as set forth in the following claims.

What is claimed is:

1. A two-piece orthodontic bracket comprising:
   outer base means for securing the bracket to a tooth;
   wire gripping means;
   said outer base means including means for releasably securing the wire gripping means to said base means;
   alignment means for aligning said gripping means with said base means upon engagement of said gripping means with said base means;
   said gripping means being in the form of an inner block adapted to engage and grip the orthodontic wire, said releasably securing means being in the form of flexible tabs extending from a central portion of said base means, and said inner block includes tab receiving slots for receiving said flexible tabs; and
   said alignment means comprising a key extending from a back face of said inner block and a keyway formed within said central portion of said base means for receiving said key and providing accurate alignment upon assembly of said inner block to said outer base means; whereby said inner block is frontally inserted and positioned within said outer base means with the flexible tabs biasingly engaging said tab receiving slots, thereby enabling the easy interchangeability of inner blocks as desired without interference with adjacent teeth and any orthodontic bracket assembly mounted on the adjacent teeth.

2. A two-piece orthodontic bracket assembly according to claim 1, wherein said inner block includes a wire receiving slot having a pre-determined position and orientation on a front face of said inner block for engagement with a wire to be gripped by said gripping means, said inner block further including a channel recessed into a back face of said inner block for receiving an orthodontic pin; and said central portion of said base means includes a longitudinal slot partially extending into said tabs for receiving said orthodontic pin.

3. A two-piece orthodontic bracket according to claim 2, wherein said block includes a channel recessed into a back face of said block and disposed therin for mutual cooperative association with said longitudinal slot for engagement with said orthodontic pin.

4. A two-piece orthodontic bracket according to claim 1, wherein said outer securing means includes a shim removably insertable between said gripping means and said base means to facilitate removal of said gripping means from said base means, and to enable positioning of said inner block further away from a tooth, thus moving the orthodontic wire further outwardly away from said tooth.

5. A two-piece orthodontic bracket according to claim 4, wherein said outer securing means includes tabs extending from a central portion of said base means, and wherein said inner block includes tab receiving slots for receiving said tabs, and said tab receiving slots are bounded by ears extending from an end portion of said block and having cam surfaces for guiding said shim between said block and said central portion of said base means; and a frontal insertion of said inner block enables the gripping thereof by the tabs in the tab receiving slots of said inner block.

6. A two-piece orthodontic bracket according to claim 5, wherein said shim is bifurcated into two leg portions spaced apart to permit passage of said leg portions on opposite sides of one of said tabs, and wherein said one tab is provided with peripheral slots for engagement with said leg portions upon an insertion of said shim between said block and said central portion.

7. A two-piece orthodontic bracket according to claim 6, wherein said alignment means includes alignment pins extending from a back face of said inner block and pin receiving slots formed within said central portion of said base means, the spacing between the leg portions of said shim being sufficiently large to permit passage of said leg portions outside of said alignment pins during an insertion of said shim between said block and said central portion of said base means.

8. A two-piece orthodontic bracket according to claim 7, wherein said inner block has a front face extending between said tabs and including a wire gripping slot recessed into said front face, the spacing between said tabs being large enough to permit said slot to be positioned over a range of elevations from a bottom edge of said inner block and over a range of inclinations relative to said bottom edge.

9. A two-piece orthodontic bracket according to claim 1, wherein for each and every tooth in the dental arches of a mouth, the plane of the bisectors of each and every set of tabs of all of the bracket securing means are generally identical to the bisector plane of every other bracket securing means, regardless of the inclination of the base means of the bracket securing means relative to the teeth.

10. An orthodontic bracket comprising:

base means for securing said bracket to a tooth;

wire gripping means having the form of a block configured for resting upon said base means;

alignment means for aligning said gripping means with said base means upon engagement of said gripping means with said base means;

said base means including means for releasably securing said block to said base means, said base means including a central plate, said securing means comprising tabs extending from opposite ends of said plate, said securing means further comprising tab receiving slots located on opposite ends of said block for receiving said tabs upon engagement of block with said base means;

said central plate of said base means having an elongated aperture of which leg portions extend generally parallel to the vertical axis of said tooth upon the securing of said bracket to said tooth, said aperture having wing portions extending transversely of said leg portions, said block having a channel in a back face thereof and oriented for mating with said leg portions upon engagement of said block with said base means, and wherein said leg portions and said channel form a guide for receiving an orthodontic pin upon insertion of said pin between said block and said plate;

said wing portions of said aperture serving as keyways of said alignment means, said alignment means further comprising alignment pins extending from said back face of said block and serving as keys for nesting within said wing portions upon engagement of said block with said base means thereby aligning said block with said tooth upon the securing of said bracket to said tooth;

said block comprising a wire gripping slot disposed within a front face of said block between said tab receiving slots, there being sufficient space between said tab receiving slots to permit said wire gripping slot to be positioned over a range of elevations relative to a bottom edge of said block and over a range of inclinations relative to said bottom edge, and wherein said tab receiving slots are bounded by ears extending from end portions of said block and having cam surfaces for guiding a shim adapted to be releasably inserted between said block and said plate of said base means for separating said block from said plate; and wherein said tabs terminating in ears oriented for engagement with an external band for urging said tabs into said tab receiving slots for securing said wire gripping means to said base means.

11. An orthodontic bracket according to claim 10, wherein said shim is bifurcated into two legs spaced apart to permit passage of said-shim legs on opposite sides of one of said tabs and on opposite sides of said alignment pins, said one tab being provided with peripheral slots for engagement with said shim legs upon insertion of said shim between said wire gripping means and said base means.

12. A two-piece orthodontic bracket according to claim 1, wherein said inner block including vertical channels on a front face thereof for receipt of at least one ligating band, and a wire receiving slot having a predetermined orientation for development of a torque by such wire, and said channels crossing said slot to permit engagement of said wire by said at least one ligating band.

13. A two-piece orthodontic bracket according to claim 12, wherein upper and lower surfaces of said block are inclined relative to each other to mate with said securing means of said base for a snap-in action in the operation of said securing means.

14. A two-piece orthodontic bracket according to claim 12, wherein said securing means includes means for engaging with said band, said engaging means being disposed above and below said channels on said front face.

* * * * *